United States Patent [19]

Chiswell

[11] Patent Number: 4,716,106
[45] Date of Patent: Dec. 29, 1987

[54] DETECTING POLYNUCLEOTIDE SEQUENCES

[75] Inventor: David J. Chiswell, Aylesbury, England

[73] Assignee: Amersham International plc, Buckinghamshire, England

[21] Appl. No.: 706,747

[22] Filed: Feb. 28, 1985

[30] Foreign Application Priority Data

Mar. 1, 1984 [GB] United Kingdom ............... 8405437

[51] Int. Cl.$^4$ .................. C12Q 1/70; C12Q 1/68; G01N 33/566
[52] U.S. Cl. ................................. 435/6; 435/5; 436/501; 536/26; 536/27; 536/28; 935/77; 935/78
[58] Field of Search .............. 435/5, 6; 436/501; 935/78, 77; 536/26, 27, 28

[56] References Cited

FOREIGN PATENT DOCUMENTS

WO84/03520 9/1984 PCT Int'l Appl. .

OTHER PUBLICATIONS

Dunn, A. R. et al., Methods in Enzymology, 65: 468–478, (1980).

*Primary Examiner*—Robert J. Warden
*Assistant Examiner*—Jack Spiegel
*Attorney, Agent, or Firm*—Wenderoth, Lind & Ponack

[57] ABSTRACT

A method of detecting a target polynucleotide sequence in a sample uses a labelled polynucleotide secondary probe, and a polynucleotide primary probe having sequences complementary to both the target and the secondary probe. The sample, immobilized or in solution is hybridized with the primary probe; and the labelled secondary probe is also hybridized with the primary probe. The method permits the production of a labelled secondary probe which can be used in conjuction with many different primary probes for different hybridization reactions.

10 Claims, 1 Drawing Figure

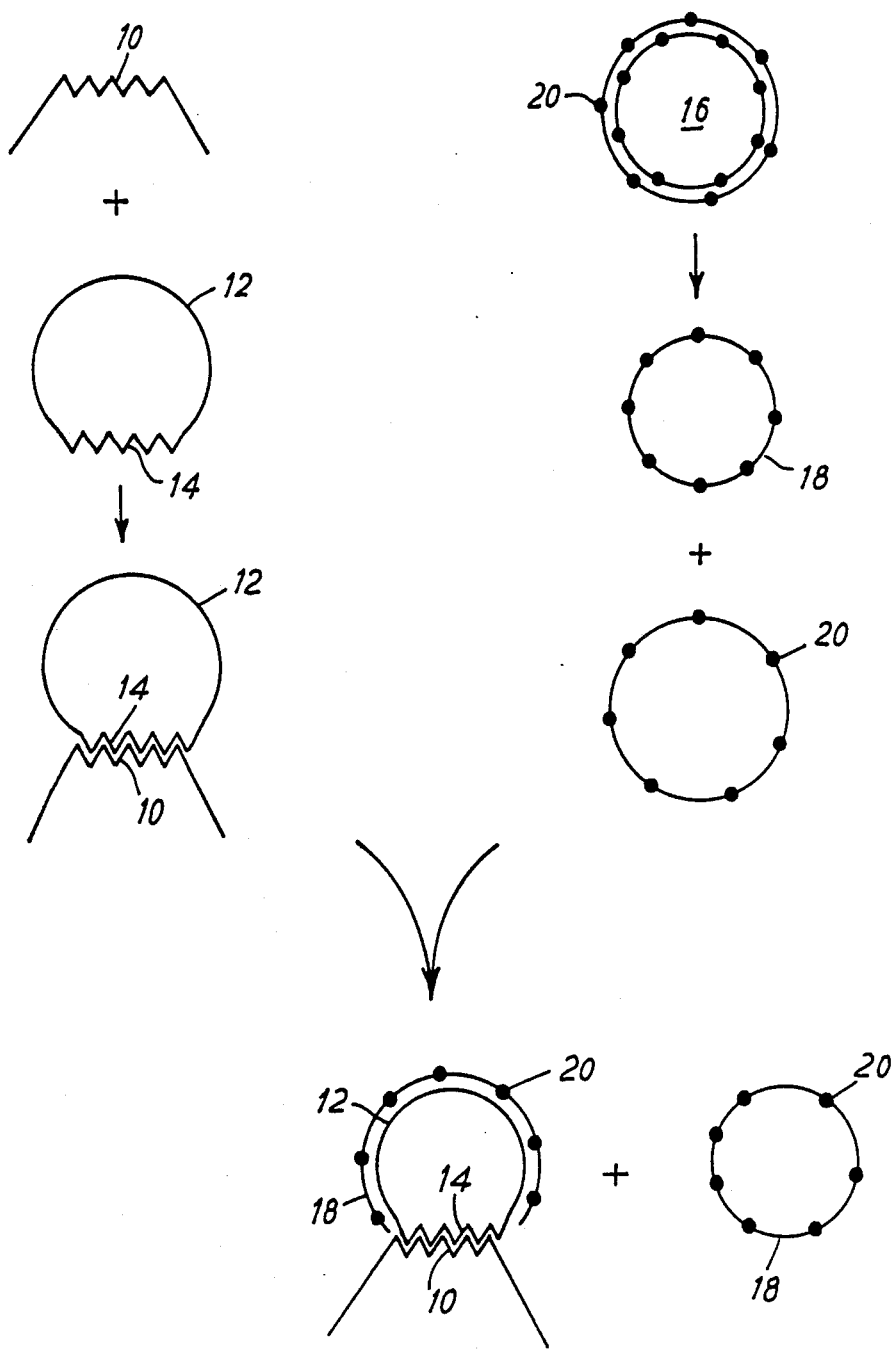

DETECTING POLYNUCLEOTIDE SEQUENCES

The detection of specific target polynucleotide sequences by their ability to hybridise to a complementary labelled probe is a crucial aspect of molecular biology. The classical method, which is still the most widely used, is to provide a 32-P-radiolabelled single-stranded polynucleotide probe, contact a sample possibly containing the target sequence under hybridisation conditions with the labelled probe, remove unreacted labelled probe, and observe the presence or absence of the label in association with the sample. For ease of separating reacted from unreacted probe, the sample is usually immobilised e.g. on a nitrocellulose filter. A large number of variations and improvements of this technique have been proposed, among which may be mentioned the following.

J. E. Manning et al [Chromasoma (Berl.), 53, 107–117 (1975)] covalently attached biotin to RNA via cytochrome c bridges. The chemically modified RNA was used as a probe. After hybridisation to the target, the biotin label was observed by means of polymethacrylate microspheres coated with avidin, which microspheres were visible in the scanning electron microscope. The technique had the advantage of avoiding the use of radioactive materials. But the label system was complex and the technique has not, so far as is known, been used commercially.

M. Renz (EMBO J. Vol. 2 pp 817–822 (1983)) covalently attached biotin to single-stranded DNA via histone H1 bridges. When used as a probe, the biotin label could be detected by an avidin-peroxidase complex.

Institut Pasteur (British Patent Specification No. 2019408) used the Manning technique (described above) as the basis of an enzyme assay for a specific target polynucleotide sequence. The coupling of an enzyme label to the probe by means of an avidin-enzyme complex, whereby the avidin bonds to biotin, is described.

Standard Oil Company (European Patent Specification No. 70687) describe an assay for a target single-stranded polynucleotide using a light-labelled probe, but do not say how the probe is made.

Yale University (European Patent Specification No. 63879) desribes a method by which biotin may be joined to a nucleotide. The resulting modified nucleotide can then be incorporated in a polynucleotide chain for use as a labelled probe for detecting a complementary target polynucleotide sequence.

Hu and Messing (GENE Vol. 17 (1982) pp 271–277) describe a method for the preparation of radiolabelled M13 probes. The probe sequence was inserted into single-stranded M13 phage. DNA synthesis of the complementary strand was initiated using radiolabelled nucleotides, but did not proceed to completion so that the probe sequence remained single-stranded.

Orion Corporation (European Patent Specification No. 79139) describe an assay for a single-stranded target involving the use of two probes, one immobilised and the other labelled. Each probe hybridises with a different polynucleotide sequence of the target. The presence of immobilised label in the hybridisation mixture indicates the presence of the single-stranded target in the assay sample.

Han and Harding (Nucleic Acids Research, 11, 7 (1983), 2053–64) describe the use of a 125-I labelled single-stranded M13 clone as a probe to identify M13 subclones.

All these prior workers used a labelled single-stranded polynucleotide probe to hybridise with the target sequence. Each probe for each different assay has to be labelled separately. Labelling of the probe necessarily involves an additional preparative step, and one which may in some cases be difficult. The present invention seeks to avoid this problem by the use of a labelled secondary probe which does not have to be complementary to the target sequence and can therefore be used in assays for a variety of different targets.

It would in principle be possible to provide a primary probe to hybridise to the polynucleotide target sequence, and a labelled secondary probe to be subsequently attached to the primary probe by homopolymer tailing or sticky-ended tails or blunt-ended ligation. But such methods are unsatisfactory, for they require complex steps to be performed under carefully controlled conditions, and form no part of this invention.

The present invention provides a method of detecting a specific target polynucleotide sequence in a sample, comprising the use of (a) a labelled polynucleotide secondary probe having a complex single-stranded polynucleotide sequence, and (b) a polynucleotide primary probe having a single-stranded sequence complementary to the target and a complex single-stranded sequence complementary to the complex sequence of the secondary probe, which method comprises the steps of (i) contacting the sample under hybridisation conditions with the primary probe, (ii) before, during or after said contact, hybridising the labelled secondary probe to the primary probe, and (iii) observing the presence or absence of the label in association with the sample as indicating the presence or absence of the target sequence.

The accompanying drawing is a diagram showing one way of performing this method.

A complex polynucleotide sequence is a sequence containing two or more, generally all four, nucleotides arranged in a non-uniform order. All naturally occurring DNA and RNA is made up of complex sequences. A homopolymer tail is not a complex sequence.

Step (i) of the method involves contacting the sample under hybridising conditions with the primary probe. If the sample contains the specific target polynucleotide sequence, this will hybridise with the complementary single-stranded sequence of the primary probe. The target sequence is long enough to permit hybridisation, i.e. generally contains more than 10 nucleotides, and may be as long as desired.

Techniques for synthesising or otherwise obtaining a single-stranded polynucleotide sequence for the primary probe, which is complementary to the target sequence, are well known in the art and will not be described here. Having been obtained, this primary probe sequence often needs to be purified and reproduced. According to a preferred feature of the invention, this may be achieved by ligating the probe section into a single-stranded DNA vector such as the phage M13 and cloning the vector in a suitable microorganism. The resulting single-stranded DNA vector contains a sequence complementary to the target, and a sequence complementary to the secondary probe (all or part of the remainder of the vector), and can be used unchanged as the primary probe. If desired, however, the vector can be linearised or divided into fragments by means of a restriction enzyme. Or the probe sequence can be removed from the vector and introduced into some other complex polynucleotide sequence.

While the primary probe is preferably single-stranded, it can be partly or wholly double-stranded. If initially wholly double stranded, the primary probe must be converted into single-stranded form, e.g. by (heat) denaturation, prior to contact with the sample. A partly double-stranded primary probe may not need to be denatured if the single-stranded sequences complementary to the target and to the secondary probe are present.

The secondary probe includes a complex single-stranded polynucleotide sequence complementary to part of the primary probe. When the primary probe is based on a single-stranded DNA vector such as M13, the secondary probe may be derived from a replicative double-stranded form of the vector, which may be converted to single-stranded form, e.g. by denaturing, immediately prior to use. When the primary probe is of RNA, the secondary probe may include a complementary DNA sequence. When the primary probe is of DNA, the secondary probe may advantageously be of RNA; a method for the production of RNA probes has recently been published (Journal Cell. Vol. 32 (1983) pp 681–694, Green M. R., Maniatis T. and Melton D. A.).

The secondary probe is labelled. By this is meant that the probe is isotopically or chemically modified in such a way that the person performing the assay can, after further manipulation if necessary, detect the presence of the secondary probe. The nature of the label is not critical; it may be a radioactive atom or a component of an enzyme or fluorescent or chemiluminescent system, or merely a chemical group by means of which such a component may subsequently be added. Techniques for labelling polynucleotides are well known and will not be described here; some are described in the prior art references discussed above. The single-stranded sequence of the secondary probe that is complementary to the primary probe may, but need not be, labelled. The labelled part of the secondary probe can be partly or wholly double-stranded.

The single-stranded sequence of the secondary probe that is complementary to the primary probe should be long enough, e.g. at least 14 nucleotides, to hybridise strongly with the primary probe, and may be as long as desired. The labelled part of the secondary probe should be long enough to carry a sufficient amount of label. Preferably, the secondary probe is labelled, and is complementary to the primary probe, along its entire length.

The labelled secondary probe can be used in conjunction with any primary probe having a suitable complex single-stranded complementary sequence. Thus the secondary probe can be based on a stock polynucleotide and labelled in bulk for use in assays for a large number of different target polynucleotide sequences.

There follow descriptions, by way of example, of various assay techniques according to the invention.

(a) Reference is directed to the accompanying drawing. The sample, including a target sequence 10, is immobilised by conventional means. In this state, it is contacted under hybridising conditions with a solution of a probe 12 which is a single stranded vector (e.g. one based on M13) with the probe sequence 14 (complementary to the target sequence) inserted. A secondary probe 18 has been formed by radioactively (or otherwise) labelling a double-stranded form 16 of the vector (e.g. M13), by conventional means (the label being shown as spots 20), and then denaturing the double stranded structure immediately prior to use. After excess unreacted primary probe has, if desired, been removed by washing, the sample is contacted, again under hybridising conditions, with a solution of this labelled secondary probe. Some of the single strands re-hybridise to one another, but others 18 bind to the primary probe attached to the immobilised sample. Label not attached to the sample is removed by washing. Thereafter, the presence or absence of label attached to the sample is observed as indicating the presence or absence of the target sequence in the sample.

(b) The reagents are as in (a), but the solution of the secondary probe is first mixed under hybridising conditions with the solution of the primary probe.

The immobilised sample is contacted with the resulting mixture. After hybridisation, excess unreacted label not attached to the sample is removed by washing. This may be an attractive alternative to (a), provided that the conditions necessary to hybridise the primary probe to the target sequence do not cause loss of label from the secondary probe.

(c) The primary probe is derived from a double-stranded DNA vector containing the probe sequence. This is denatured, and optionally also subjected to a restriction enzyme, just prior to use. The resulting solution contains a variety of single-stranded DNA chains, some or all of which include the probe sequence. When the immobilised sample is contacted with this solution under hybridising conditions, the probe sequence becomes hybridised to the target sequence and partial re-hybridisation of the probe takes place, resulting in an immobilised probe that is partly single-stranded and partly double-stranded. The labelled secondary probe is then caused to hybridise to these single-stranded portions.

(d) Alternatively, a solution of the labelled secondary probe can be added to the solution of single-stranded DNA chains before, rather than after, contact with the immobilised sample.

(e) The primary probe is derived from a double-stranded DNA vector containing the probe sequence. The secondary probe is derived from a corresponding double-stranded DNA vector which has been labelled. A mixture of the two probes is first denatured, and then added under hybridising conditions to the immobilised sample. Some of the primary probe becomes hybridised to the target and some of the secondary probe becomes hybridised to the primary probe.

While this arrangement is relatively inefficient because of the substantial amount of re-hybridisation that inevitably takes place, it does have the advantage of using primary and secondary probes derived from double-stranded DNA.

(f) It is possible also to perform the method with the target sequence in solution. Indeed, this may result in a useful improvement in efficiency of the hybridising reactions. Thus, the sample including the target sequence is contacted under hybridising conditions with a solution of a single-stranded primary probe. The solution is subjected to hydroxylapatite chromatography to separate partially double-stranded sequences (primary probe hybridised to target) from single-stranded sequences (primary probe not hybridised). The solution containing partially double-stranded sequences is then contacted under hybridising conditions with a solution of the labelled single-stranded secondary probe. Remaining single-stranded sequences are broken down into single nucleotides by an enzyme such as S1 nuclease and removed. Thereafter the presence or absence of label in the solution is observed as indicating the presence or absence of the target sequence in the sample.

Other techniques for performing the test in solution will readily occur to the skilled reader. Techniques may include variants of those noted above as (a) to (e), may use known separation techniques based on hydroxylapatite chromatography or other separation media and/or on S1 nuclease or other hydrolysing enzymes particularly those specific for single-stranded polynucleotides, and may involve RNA probes.

The following Example illustrates the invention. The method is that described under (a) above.

Materials

Target DNA: Human placental lactagen (HPL) specific DNA cloned into plasmid vector pAT 153 (pHPL).

Primary probe: HPL specific DNA cloned into the bacteriophage vector M13 [M13 (HPL)]; this gives a single stranded DNA with both HPL and phage M13 specific sequences.

Secondary probe: Replicative (double stranded) form of phage M13 DNA (M13RF) labelled with [$^{32}$P] using standard nick-translation procedure. (This probe will hybridise with the M13 portion of the primary probe).

Hybridisation solution: 6×SSC (1×SSC=0.15M Sodium Chloride, 0.015M Sodium Citrate); 50 ug/ml calf thymus DNA (Sonicated and Denatured); 0.1% Sodium dodecyl Sulphate (SDS); 5×Denhardts solution (0.1% Ficoll, 0.1% Bovine Serum Albumen, 0.1% Polyvinylpyrrolidone); 10% Dextran Sulphate.

Method 40 pg of pHPL (i.e. equivalent to the level of HPL DNA in 10 ug of human genomic DNA) was run on an agarose gel and transferred to nitrocellulose using standard techniques. After baking two identical nitrocellulose filters containing the pHPL DNA at 80° for 2 hours they were soaked in 2×SSC, then placed at 65° in hybridisation solution for 2 hours. Filter (a) was then placed in 5 mls of fresh hybridisation solution in a resealed bag, filter (b) was similarly sealed inside a bag containing 5 mls of fresh hybridisation solution plus 2 ug of M13 (HPL) DNA. Both bags were incubated at 65° for a further two hours. Both filters were then washed twice for 15 minutes at 65° in approximately 50 mls of 2×SSC containing 0.1% SDS. They were then incubated for 16 hours at 65° in 25 mls of hybridisation solution into which 100 ng of heat denatured M13RF labelled with $^{32}$P (specific activity approximately 1+10$^8$ cpm/microgram) had just been added. Both filters were then washed at 65° for 30 minutes in 2×SSC plus 0.1% SDS (2×30 minute washes) followed by 0.1×SSC plus 0.1% SDS (2×30 minute washes). They were then dried and autoradiographed. When the autoradiographic films were developed a band was observed on filter (b) [but not on filter (a)] corresponding to the position of the pHPL DNA.

This demonstrates that the pHPL DNA is being detected by a complex of the pimary and secondary probes.

I claim:

1. A method of detecting a specific target polynucleotide sequence in a sample, comprising the use of (a) a labelled polynucleotide secondary probe having a complex single-stranded polynucleotide sequence, and
    (b) a polynucleotide primary probe having a single-stranded sequence complementary to the target sequence and a complex single-stranded sequence complementary to the complex sequence of the secondary probe, which method comprises the steps of (i) contacting the sample under hybridisation conditions with the primary probe,
    (ii) before, during or after said contact hybridising the labelled secondary probe to the primary probe, and
    (iii) observing the presence or absence of the label in association with the sample as indicating the presence or absence of the target sequence.

2. A method as claimed in claim 1, wherein the sample is immobilised on a solid support.

3. A method as claimed in claim 2, wherein the sample is contacted first with the primary probe and subsequently with the secondary probe.

4. A method as claimed in claim 2, wherein a solution of the secondary probe is first mixed under hybridising conditions with a solution of the primary probe and the immobilised sample is contacted with the resulting mixture.

5. A method as claimed in claim 3, wherein the primary probe is derived from a double-stranded DNA vector containing the single-stranded sequence complementary to the target which is denatured just prior to use.

6. A method as claimed in claim 4, wherein the primary probe is derived from a double-stranded DNA vector containing the single-stranded sequence complementary to the target which is denatured just prior to use.

7. A method as claimed in claim 2, wherein the primary probe is derived from a double-stranded DNA vector containing the single-stranded sequence complementary to the target, the secondary probe is derived from a corresponding double-stranded DNA vector which has been labelled, and a mixture of the two probes is first denatured and then added under hybridising conditions to the immobilised sample.

8. A method as claimed in claim 1, wherein a solution of the sample is contacted under hybridising conditions with a solution of a single-stranded primary probe, a solution containing partly double-stranded sequences but not single-stranded sequences is recovered and contacted under hybridising conditions with a solution of a labelled single-stranded secondary probe, remaining single-stranded sequences are removed, and the presence or absence of label in association with the sample is observed as indicating the presence or absence of the target sequence in the sample.

9. A method as claimed in claim 1, wherein the primary probe is based on a single-stranded plasmid or bacteriophage and the secondary probe is derived from a replicative double-stranded form of the bacteriophage.

10. A method as claimed in claim 1, wherein the primary probe is of DNA and the secondary probe is of RNA.

* * * * *